(12) United States Patent
Susak et al.

(10) Patent No.: US 8,765,156 B2
(45) Date of Patent: Jul. 1, 2014

US008765156B2

(54) TOPICAL COMPOSITIONS COMPRISING INORGANIC PARTICULATES AND AN ALKOXYLATED DIPHENYLACRYLATE COMPOUND

(75) Inventors: Milanka Susak, North York (CA); Ismail Ahmed Syed, Ronkonkoma, NY (US); Linda Josephine Najdek, East Islip, NY (US); Mirela Cristina Ionita-Manzatu, Old Bethpage, NY (US)

(73) Assignee: ELC Management LLC, New York, NY (US)

( * ) Notice: Subject to any disclaimer, the term of this patent is extended or adjusted under 35 U.S.C. 154(b) by 0 days.

(21) Appl. No.: 12/771,237

(22) Filed: Apr. 30, 2010

(65) Prior Publication Data

US 2011/0110988 A1 May 12, 2011

Related U.S. Application Data

(60) Provisional application No. 61/175,261, filed on May 4, 2009.

(51) Int. Cl.
*A61K 8/02* (2006.01)
*A61K 8/00* (2006.01)
*A61Q 17/04* (2006.01)
*A61K 33/24* (2006.01)
*A61K 9/50* (2006.01)
*A61K 8/27* (2006.01)
*A61K 47/32* (2006.01)
*A61K 47/24* (2006.01)
*A61K 8/40* (2006.01)
*A61K 31/12* (2006.01)
*A61K 33/30* (2006.01)
*A61K 8/29* (2006.01)
*A61K 9/00* (2006.01)
*A61K 47/10* (2006.01)
*A61K 47/06* (2006.01)

(52) U.S. Cl.
CPC ............... *A61K 31/12* (2013.01); *A61K 33/24* (2013.01); *A61K 9/5026* (2013.01); *A61K 8/27* (2013.01); *A61K 47/32* (2013.01); *A61K 47/24* (2013.01); *A61K 8/40* (2013.01); *A61Q 17/04* (2013.01); *A61K 33/30* (2013.01); *A61K 8/29* (2013.01); *A61K 9/0014* (2013.01); *A61K 47/10* (2013.01); *A61K 47/06* (2013.01)
USPC ............................................. 424/401; 424/60

(58) Field of Classification Search
USPC ................................................... 424/401, 60
See application file for complete search history.

(56) References Cited

U.S. PATENT DOCUMENTS

| | | | |
|---|---|---|---|
| 3,215,724 A | 11/1965 | Strobel et al. | |
| 3,439,088 A | 4/1969 | Edman | |
| 3,781,417 A | 12/1973 | Welters et al. | |
| 3,818,105 A | 6/1974 | Coopersmith et al. | |
| 4,677,152 A | 6/1987 | Allen et al. | |
| 4,702,844 A | 10/1987 | Flesher et al. | |
| 4,803,067 A | 2/1989 | Brunetta et al. | |
| 4,889,845 A | 12/1989 | Ritter et al. | |
| 4,970,252 A | 11/1990 | Sakuta et al. | |
| 5,077,211 A | 12/1991 | Yarosh | |
| 5,118,496 A | 6/1992 | Herstein | |
| 5,183,588 A | 2/1993 | Salerno et al. | |
| 5,183,589 A | 2/1993 | Brunetta et al. | |
| 5,190,762 A | 3/1993 | Yarosh | |
| 5,236,986 A | 8/1993 | Sakuta | |
| 5,272,079 A | 12/1993 | Yarosh | |
| 5,296,231 A | 3/1994 | Yarosh | |
| 5,412,004 A | 5/1995 | Tachibana et al. | |
| 5,576,354 A | 11/1996 | Deflandre et al. | |
| 5,654,362 A | 8/1997 | Schulz, Jr. et al. | |
| 5,760,116 A | 6/1998 | Kilgour et al. | |
| 5,811,487 A | 9/1998 | Schulz, Jr. et al. | |
| 5,837,793 A | 11/1998 | Harashima et al. | |
| 5,843,193 A | 12/1998 | Hawkins et al. | |
| 5,928,629 A | 7/1999 | Allard et al. | |
| 5,955,091 A | 9/1999 | Hansenne | |
| 5,989,528 A | 11/1999 | Tanner et al. | |
| 6,146,617 A | 11/2000 | Kurz et al. | |
| 6,146,649 A * | 11/2000 | Hansenne | 424/401 |
| 6,342,209 B1 | 1/2002 | Patil et al. | |

(Continued)

FOREIGN PATENT DOCUMENTS

CA 2642783 9/2007
EP 1 153 600 11/2001

(Continued)

OTHER PUBLICATIONS

Bonda, Cosmetics & Toiletries, 123 (2), 49, 50, 52-58 and 60; published: Feb. 2008.*

Bonda, Craig; Research Pathways to Photostable Sunscreens; Cosmetic & Toiletries®; The International Magazine of Cosmetic Technology; Innovation Through Interaction; vol. 123; No. 2; www.CosmeticsandToiletries.com; Feb. 2008. (11 submitted pages).

PCT International Search Report; International Application No. PCT/US2010/033328; Completion Date: Dec. 14, 2010; Date of Mailing: Dec. 14, 2010.

(Continued)

*Primary Examiner* — Gina C Justice
*Assistant Examiner* — Genevieve S Alley
(74) *Attorney, Agent, or Firm* — Idris N. McKelvey

(57) ABSTRACT

A topical composition of improved spreadability and aesthetical appeal is provided, which contains inorganic particulates in combination with an alkoxylated diphenylacrylate compound. Preferably, the topical composition is a sunscreen composition that contains inorganic or physical sunscreen agents in combination with an alkoxylated α-cyanodiphenylacrylate compound, which is characterized by improved photo-protection of the skin and is effective in preventing/reducing photo-damage of the skin upon exposure to sunlight or other sources of light in the ultraviolet (UV), visible, and infrared (IR) ranges.

15 Claims, No Drawings

(56) References Cited

U.S. PATENT DOCUMENTS

| | | | |
|---|---|---|---|
| 6,776,980 B1* | 8/2004 | Allard et al. | 424/59 |
| 6,936,241 B2 | 8/2005 | Yamada et al. | |
| 6,964,773 B1 | 11/2005 | Morrison | |
| 7,083,800 B1 | 8/2006 | Terren et al. | |
| 7,166,275 B2 | 1/2007 | Bertz et al. | |
| 7,357,919 B2 | 4/2008 | Candau | |
| 7,368,105 B2 | 5/2008 | Candau | |
| 7,666,442 B2 | 2/2010 | Morariu | |
| 8,075,808 B2 | 12/2011 | Bonda et al. | |
| 8,088,364 B2 | 1/2012 | Breyfogle et al. | |
| 2001/0028888 A1 | 10/2001 | Heidenfelder et al. | |
| 2002/0086042 A1* | 7/2002 | Delrieu et al. | 424/401 |
| 2003/0228339 A1* | 12/2003 | El-Nokaly et al. | 424/401 |
| 2005/0019280 A1 | 1/2005 | Bertz et al. | |
| 2005/0186153 A1* | 8/2005 | Bonda et al. | 424/59 |
| 2006/0034875 A1 | 2/2006 | Nakanishi et al. | |
| 2006/0078514 A1 | 4/2006 | Bertz et al. | |
| 2006/0147505 A1 | 7/2006 | Tanzer et al. | |
| 2006/0280712 A1* | 12/2006 | Kuroda et al. | 424/70.12 |
| 2007/0207113 A1 | 9/2007 | Joerger et al. | |
| 2009/0039322 A1 | 2/2009 | Bonda et al. | |
| 2009/0039323 A1 | 2/2009 | Bonda et al. | |
| 2009/0041847 A1 | 2/2009 | Bonda et al. | |
| 2009/0042312 A1 | 2/2009 | Bonda | |
| 2009/0057627 A1 | 3/2009 | Bonda et al. | |
| 2009/0074687 A1 | 3/2009 | Bonda et al. | |
| 2009/0155371 A1 | 6/2009 | Sojka et al. | |

FOREIGN PATENT DOCUMENTS

| | | |
|---|---|---|
| EP | 1819315 | 8/2007 |
| EP | 2 025 324 | 2/2009 |
| JP | 61-018708 | 1/1986 |
| JP | 11-514670 | 12/1999 |
| JP | 2000-026262 | 1/2000 |
| JP | 2000-191490 | 7/2000 |
| JP | 2001-240525 | 9/2001 |
| JP | 3658561 | 6/2005 |
| JP | 2007-145859 | 6/2007 |
| KR | 20000022115 | 4/2000 |
| WO | WO98/50000 | 11/1998 |
| WO | WO2004/024798 | 3/2004 |
| WO | WO2005/009341 | 2/2005 |
| WO | WO2006/087066 | 8/2006 |
| WO | WO2007/133769 | 11/2007 |
| WO | WO2009/020675 | 2/2009 |
| WO | WO2009/020676 | 2/2009 |

OTHER PUBLICATIONS

PCT Written Opinion of the International Searching Authority, or The Declaration; International Application No. PCT/US2010/033328; Completion Date: Dec. 14, 2010; Mailing Date: Dec. 14, 2010.

PCT International Search Report; International Application No. PCT/US2010/032677; Completion Date: Jan. 19, 2011; Date of Mailing: Jan. 21, 2011.

PCT Written Opinion of the International Searching Authority, or The Declaration; International Application No. PCT/US2010/032677; Completion Date: Jan. 19, 2011; Mailing Date: Jan. 21, 2011.

PCT International Search Report; International Application No. PCT/US2010/032683; Completion Date: Jan. 19, 2011; Date of Mailing: Jan. 21, 2011.

PCT Written Opinion of the International Searching Authority, or The Declaration; International Application No. PCT/US2010/032683; Completion Date: Jan. 19, 2011; Mailing Date: Jan. 21, 2011.

PCT International Search Report; International Application No. PCT/US2010/032692; Completion Date: Dec. 14, 2010; Date of Mailing: Jan. 3, 2011.

PCT Written Opinion of the International Searching Authority, or The Declaration; International Application No. PCT/US2010/032692; Completion Date: Dec. 14, 2010; Mailing Date: Jan. 3, 2011.

PCT International Search Report; International Application No. PCT/US2010/032702; Completion Date Dec. 15, 2010; Date of Mailing: Jan. 3, 2011.

PCT Written Opinion of the International Searching Authority, or The Declaration; International Application No. PCT/US2010/032702; Completion Date: Dec. 15, 2010, Mailing Date: Jan. 3, 2011.

Supplementary European Search Report Applic. No. EP10772557.4; Completion Date: Aug. 23, 2012, Date of Mailing: Aug. 31, 2012.

Newton, et al.; Silicone Technology Offers Novel Methods for Delivering Active Ingredients; SOFW Journal; 130(5); pp. 8-13; Downloaded from : http://www3.dowcorning.com/content/publishedlit/27-1153-01.pdf on Oct. 23, 2013.

* cited by examiner

TOPICAL COMPOSITIONS COMPRISING INORGANIC PARTICULATES AND AN ALKOXYLATED DIPHENYLACRYLATE COMPOUND

CROSS-REFERENCE TO RELATED APPLICATIONS

This claims priority to U.S. Provisional Patent Application No. 61/175,261 filed May 4, 2009.

FIELD OF THE INVENTION

The invention relates to topical compositions with skin care or cosmetic properties. Specifically, the invention relates to topical compositions containing inorganic particulates in combination with an alkoxylated diphenylacrylate compound, which functions to improve dispersion (i.e., reduced coagulation) of the inorganic particulates and thereby achieve better feel/spreadability of such compositions on the skin. More specifically, when the inorganic particulates are physical sunscreen particles, such as titanium dioxide and/or zinc oxide particles, the topical compositions of the present invention are characterized by enhanced photo-protection and are particularly useful for preventing/reducing photo-damage of the skin upon exposure to sunlight or other sources of light in the ultraviolet (UV), visible, and infrared (IR) ranges.

SUMMARY OF THE INVENTION

The present invention provides a topical composition comprising at least one inorganic particulate material and a diphenylacrylate, more specifically an alkoxylated diphenylacrylate compound, in a pharmaceutically or cosmetically acceptable carrier. It has been discovered that the alkoxylated diphenylacrylate compound, which is a lipophilic organic compound, surprisingly and unexpectedly improves dispersion of the inorganic particulate material in the pharmaceutically or cosmetically acceptable carrier and reduces potential agglomeration.

In a preferred, but not necessary, embodiment, the present invention provides a topical sunscreen composition for protecting the skin against photo-damage upon exposure to UV radiation, which comprises at least one physical sunscreen agent selected from the group consisting of titanium dioxide and zinc oxide and an alkoxylated α-cyanodiphenylacrylate compound in a pharmaceutically or cosmetically acceptable carrier. The alkoxylated α-cyanodiphenylacrylate compound preferably has the formula (I):

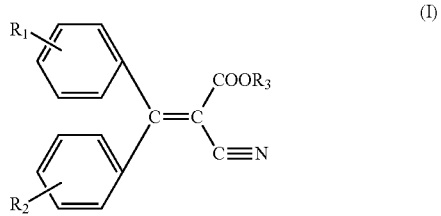

wherein one or both of $R_1$ and $R_2$ is a straight or branched-chain $C_1$-$C_{30}$ alkoxy radical, any non-alkoxy radical $R_1$ or $R_2$ is hydrogen, and $R_3$ is a straight or branched-chain $C_1$-$C_{30}$ alkyl radical. It has been discovered that such an alkoxylated α-cyanodiphenylacrylate compound, when combined with a physical sunscreen agent, surprisingly and unexpectedly enhances the photo-protective effect of the physical sunscreen agent, even in absence of any chemical sunscreen agent. Therefore, in a most preferred embodiment, the topical sunscreen composition of the present invention is substantially free of chemical sunscreen agents, such as, for example, dibenzoylmethane compounds or derivatives thereof.

DETAILED DESCRIPTION OF THE INVENTION, AND THE PREFERRED EMBODIMENTS THEREOF

The term "percentage" or "%" as used herein in connection with the amount or concentration of an ingredient or component in a composition refers to the percentage by total weight of the final composition, unless otherwise specified.

The term "substantially free of" or "in absence of" as used herein refers to an amount that is equal to or less than 1% by total weight of the final composition.

The inventors of the present invention discovered that α-cyanodiphenylacrylate compounds are effective in facilitating the dispersion of inorganic particulates and improving the overall aesthetical appeal of the resulting topical composition (e.g., feel and spreadability on skin). This discovery is particularly surprising and unexpected in light of the fact that the inorganic particulates, such as metal oxides, are highly charged particles, while the α-cyanodiphenylacrylate compounds are lipophilic organic compounds.

Furthermore, the inventors discovered that when the inorganic particulates are physical sunscreen agents, such as titanium dioxide and/or zinc oxide particles, the combination thereof with the α-cyanodiphenylacrylate compound surprisingly and unexpectedly enhances the efficacy of the overall composition in protecting the skin against UV-induced damages, even in absence of any chemical sunscreen agents, such as butyl methoxydibenzoylmethane (hereinafter "Avobenzone") and/or octyl methoxycinnamate (hereinafter "OMC").

Any inorganic particulate material suitable for topical application can be used in the present invention, which include, but are not limited to titanium dioxide, zinc oxide, iron oxides, mica, titanated mica, alumina, talc, pearl powder, calcium carbonate, calcium phosphate, calcium silicate, calcium sulfate (gypsum), magnesium carbonate, magnesium oxide, magnesium silicate, magnesium aluminum silicate, magnesium trisilicate, aluminum silicate, aluminum magnesium silicate, silica, fumed silica, hydrated silica, spherical silica, silica silylate, bismuth oxychloride, chalk, kaolin, diatomaceous earth, fuller's earth, kaolin, sericite, muscovite, phlogopite, lepidolite, biotite, vermiculite, smectite clays, strontium silicate, metal tungstate, magnesium, silica alumina, zeolite, tin oxide, barium sulfate, fluorine apatite, hydroxyapatite, ceramic powder, colloidal silicone dioxide, boron nitride, hectorite, montmorillonite, bentonite, attapulgite, titanium hydroxide, trimagnesium phosphate, and the like.

Preferred inorganic particulate materials are selected from metal oxides, such as titanium dioxide, zinc oxide, iron oxides, magnesium oxide, alumina (or aluminum oxide), tin oxide, and the like. More preferably, the topical composition of the present invention is a sunscreen composition that comprises at least one inorganic sunscreen agent, such as titanium dioxide and zinc oxide, and most preferably, it comprises a blend of titanium dioxide and zinc oxide.

The average particle size of the inorganic particulate materials is preferably less than 1 micron, more preferably ranging from about 0.001 micron to about 0.9 micron, and most preferably from about 0.1 to about 0.5 micron. The inorganic particulate materials of the present invention can be of any regular or irregular shape, such as, for example, spherical, cubic, cylindrical, planar, fibrous, and the like. Such inorganic particulate materials may either be naked (i.e., uncoated) or be surface-treated or coated with one or more layers of coating materials to impart desirable surface properties thereto. For example, the inorganic particulate materials may be coated with a hydrophilic or hydrophobic polymer, or encapsulated/entrapped in a hydrophilic or hydrophobic polymeric matrix, to improve the compatibility of such inorganic particulate materials with the carrier medium.

In a preferred, but not necessary embodiment of the present invention, the inorganic particulate materials are entrapped in a collapsed polymeric shell to form microspheres having an average particle size ranging from about 1 micron to about 50 microns. The collapsed polymeric shell can be formed of any synthetic or natural crosslinked or un-crosslinked polymer. If the polymer is crosslinked, it is preferred that it is weakly crosslinked. Preferably, but not necessarily, the collapsed polymeric shell comprises at least one synthetic polymer obtained by polymerization of one or more ethylenically unsaturated monomers to form homopolymers or copolymers of ethylenically unsaturated monomers or copolymers of ethylenically unsaturated monomers and one or more organic groups. Examples of ethylenically unsaturated monomers that may be suitable include, for example, vinylidene chloride, vinyl chloride, acrylonitrile, acrylic acid and its corresponding C1-C20 aliphatic or aromatic esters, methacrylic acid and its corresponding C1-C20 aliphatic or aromatic esters, acrylamide, methacrylamide, vinyl pyrrolidone, alkenes such as styrene, ethylene, propylene, butylene, methylpentene, 1,3-butadiene, and the like. The polymeric shells of the hollow microspheres may also be formed of suitable synthetic polymers, such as polyesters, polyamides, polyphthalamides, polyimides, polycarbonates, polyketones, cellulose acetate, polysulfones, polyphenylene sulfides, polyphenylene oxides, polylactic acids, polyvinylpyrrolidone, polystyrene, polyacrylonitrile, polyacrylamide, polymethylmethacrylate, polyacrylates, and copolymers of the above-listed polymers. In a particularly preferred embodiment, the collapsed polymeric shell is formed of a copolymer of vinylidene chloride, acrylonitrile, and/or methyl methyacrylate.

Entrapment of the inorganic particulate materials into the above-described collapsed polymeric shell can be achieved by first providing hollow microspheres with deformable polymeric shells having encapsulated therein an expandable fluid, which are then mixed with, either sequentially in any order or simultaneously, a polar organic solvent capable of swelling but not dissolving the polymeric shells of the hollow microspheres and the inorganic particulate materials to be entrapped. A gelled mixture is thereby formed, which contains microspheres with polymeric shells in a gelled state, which are sufficiently swelled so as to have micro-channels or through-holes formed therein to allow entry of the inorganic particulate materials into the microspheres. Such micro-channels or through-holes in the swelled polymeric shells of the microspheres also allow exit of the expandable fluid from the microspheres, thereby causing immediate collapse or implosion of the polymeric shells and entrapping the inorganic particulate materials inside the microspheres. Subsequently, the expandable fluid and the polar organic solvent are removed from the gelled mixture. Preferably but not necessarily, a film-forming material is coated over the collapsed polymeric shells to form a liquid-impermeable membrane thereon, which functions to isolate the collapsed polymeric shells of the microspheres from any solvent in the surrounding environment that may swell or otherwise affect the structural integrity of such polymeric shells. In this manner, the inorganic particulate materials can be securely entrapped inside the microspheres with little or no risk of leaking out. The hollow microspheres as initially provided (i.e., before mixing with the solid particles and the polar organic solvent) are preferably expandable hollow polymeric microspheres, each of which contains a deformable polymeric shell that is gas-tight and has enclosed or encapsulated therein an expandable fluid. Upon heating, the enclosed or encapsulated fluid can expand volumetrically to apply pressure on the interior wall of the deformable polymeric shell. At the same time, the elevated temperature may cause the polymeric shell to soften, thereby allowing the entire microsphere to expand in a manner similar to a balloon. For more details regarding the structure and composition of the hollow microspheres and the inorganic particulate entrapment process, see U.S. Patent Application Publication No. 2009/0155371, the content of which is incorporated herein by reference in its entirety for all purposes.

The inorganic particulate material can be present in the topical composition of the present invention in an amount ranging from about 0.1% to about 90%, preferably from about 5% to about 50%, and more preferably from about 10% to about 30%, by total weight of the composition.

Although all alkoxylated α-cyanodiphenylacrylate compounds are suitable for the practice of the present invention, preferred alkoxylated α-cyanodiphenylacrylate compounds for use in the present invention are those with an alkoxyl substitution group at the para position of at least one of the phenyl rings, i.e., those represented by formula (II):

(II)

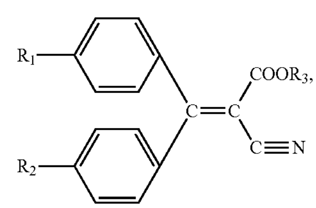

wherein one or both of $R_1$ and $R_2$ is a straight or branched-chain $C_1$-$C_{30}$ alkoxy radical, more preferably a straight or branched-chain $C_1$-$C_8$ alkoxy radical, any non-alkoxy radical $R_1$ or $R_2$ is hydrogen, and $R_3$ is a straight or branched-chain $C_1$-$C_{30}$ alkyl radical. Among straight or branched-chain $C_1$-$C_8$ alkoxy radicals, preferred are methoxy, ethoxy, n-propoxy, iospropoxy, n-butyoxy, isobutyoxy, and tert-butoxy radicals. Among straight or branched-chain $C_1$-$C_{30}$ alkyl radicals, preferred are methyl, ethyl, n-propyl, isopropyl, n-butyl, isobutyl, tert-butyl, n-amyl, isoamyl, neopentyl, n-hexyl, n-heptyl, n-octyl, 2-ethylhexyl, decyl and lauryl radicals.

More preferred species of alkoxylated α-cyanodiphenylacrylate compounds include those having the formulas (III)-(V):

(III)

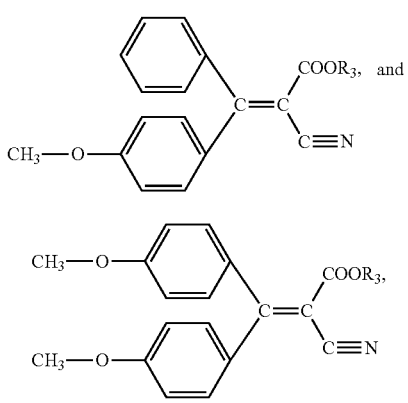

wherein R$_3$ is as previously defined.

Most preferred species of alkoxylated α-cyanodiphenylacrylate compound for the practice of the present invention is α-ethylhexyl α-cyano-β-(4-methoxyphenyl)-O-phenylacrylate (hereinafter "methoxycrylene"), which is commercially available from HallStar Company (Chicago, Ill.). Methoxycrylene has been used in the past for stabilizing certain organic or chemical sunscreen agents that are susceptible to photo-decomposition upon exposure to UV radiation, such as Avobenzone and OMC. For more details about Methoxycrylene, see U.S. Patent Application Publication Nos. US2009/039322A, US2009/039323A and US2009/042312A, and International Patent Application Publication No. WO09/020,675A, which are hereby incorporated by reference in their entireties for all purposes.

It has been discovered by the inventors that methoxycrylene is a surprisingly and unexpectedly effective dispersing agent, and it can be combined with inorganic particulate materials to form cosmetic or sunscreen compositions of excellent spreadability with little or no coagulation.

Further, it has been discovered by the inventors that methoxycrylene, when combined with physical sunscreen agents, such as TiO$_2$ or ZnO, can synergistically enhance the photoprotective effect of such physical sunscreen agents, in the absence of any organic or chemical sunscreens. Nothing in the state of art teaches, suggests or even contemplates such a synergistic effect of methoxycrylene in combination with a purely physical sunscreen system, which is both surprising and unexpected. In addition, the refractive index (RI) of methoxycrylene is significantly higher than that of its non-alkoxylated structural analogs. For example, methoxycrylene has a RI of about 1.59, while octocrylene, which is a non-alkoxylated structural analog of methoxycrylene, has a RI of only about 1.56-1.57. The higher RI value of methoxycrylene allows it to form more transparent (and therefore more aesthetically acceptable) sunscreen formulations when combined with titanium dioxide or zinc oxide, which has a RI value of above 2.

The alkoxylated diphenylacrylate compound can be present in the topical composition of the present invention in an amount ranging from about 0.01% to about 50%, preferably from about 0.1% to about 20%, and more preferably from about 1% to about 15%, by total weight of the composition.

Although not necessarily, the inorganic particulate material and the alkoxylated diphenylacrylate compound can be formulated with one or more optional organic or chemical sunscreen agents, thereby providing sunscreen compositions of high SPF values (e.g., SPF measurements of greater than 25, 30, 35, 40, 45, or even 50 or more). If present, such organic or chemical sunscreen agents may each range from about 0.01 to 45% by weight of the total composition.

Exemplary organic or chemical sunscreen agents that can be used in combination with the inorganic particulate material and the alkoxylated diphenylacrylate compound of the present invention include, but are not limited to UVA and UVB sunscreens, such as benzophenones and derivatives thereof (e.g., benzophenone-3, dioxybenzone, sulisobenzone, octabenzone, hydroxy- and/or methoxy-substituted benzophenones, and benzophenonesulfonic acids and salts thereof); salicylic acid derivatives (e.g., ethylene glycol salicylate, triethanolamine salicylate, octyl salicylate, homomethyl salicylate, and phenyl salicylate); urocanic acid and derivatives thereof (e.g., ethyl urocanate); p-aminobenzoic acid (PABA) and derivatives thereof (e.g., ethyl/isobutyl/glyceryl esters thereof and 2-ethylhexyl p-dimethylaminobenzoate, which is also referred to as octyldimethyl PABA); anthranilates and derivatives thereof (e.g., o-aminobenzoates and various esters of amino-benzoic acid); benzalmalonate derivatives; benzimidazole derivatives; imidazolines; bis-benzazolyl derivatives; dibenzoylmethanes and derivatives thereof; benzoazole/benzodiazole/benzotriazoles and derivatives thereof (e.g., 2-(2-hydroxy-5-methylphenyl) benzotriazole and methylene bis-benzotriazolyl tetramethylbutylphenol, which is commonly referred to as "Tinosorb M"); diesters or polyesters containing diphenylmethylene or 9H-fluorene substitutional groups; 2-phenyl-benzimidazole-5-sulphonic acid (PBSA); 4,4-diarylbutadienes; cinnamates and derivatives thereof (e.g., 2-ethylhexyl-p-methoxycinnamate, octyl-p-methoxycinnamate, umbelliferone, methylumbelliferone, methylaceto-umbelliferone, esculetin, methylesculetin, and daphnetin); camphors and derivatives thereof (e.g., 3-benzylidenecamphor, 4-methylbenzylidenecamphor, polyacrylamidomethyl benzylidenecamphor, benzylidene camphor sulfonic acid, and terephthalylidene dicamphor sulfonic acid, which is commonly referred to as "Encamsule"); triazines and derivatives thereof (e.g., 2,4-bis-{[4-(2-ethylhexyloxy)-2-hydroxy]-phenyl}-6-(4-methoxyphenyl)-1,3,5-triazine, which is commonly referred to as "Tinosorb S"); naphthalates and derivatives thereof (e.g., diethylhexyl-2,6-naphthalate); naphtholsulfonates and derivatives thereof (e.g., sodium salts of 2-naphthol-3,6-disulfonic and 2-naphthol-6,8-disulfonic acids); dibenzalacetone and benzalacetonephenone; diphenylbutadienes and derivatives thereof; dihydroxynaphthoic acid and salts thereof; o- and p-hydroxybiphenyldisulfonates; coumarin derivatives (e.g., 7-hydroxy, 7-methyl, and 3-phenyl derivatives thereof); azoles/diazoles/triazoles and derivatives thereof (e.g., 2-acetyl-3-bromoindazole, phenyl benzoxazole, methyl naphthoxazole, and various aryl benzotriazoles); quinine and derivatives thereof (e.g., bisulfate, sulfate, chloride, oleate, and tannate salts thereof); quinoline and derivatives thereof (e.g., 2-phenylquinoline and 8-hydroxyquinoline salts); tannic acid and derivatives thereof (e.g., hexaethylether derivatives thereof); hydroquinone and derivatives thereof; uric acid and derivatives thereof; vilouric acid and derivatives thereof, and mixtures or combinations thereof. Salts and otherwise neutralized forms of certain acidic sunscreens from the list hereinabove are also useful herein. These organic or chemical sunscreen agents may be used alone or in combination of two or more. In addition, other known animal or vegetable extracts having UV light-absorbing ability may properly be used alone or in combination.

Organic or chemical sunscreen agents that are particularly useful for the practice of the present invention are: 4,4'-t-butyl methoxydibenzoylmethane, 2-ethylhexylsalicylate, 3,3,5-trimethylcyclohexylsalicylate, 2-ethylhexyl p-methoxycinnamate, 2-hydroxy-4-methoxybenzophenone, 2,2-dihydroxy-4-methoxybenzophenone, 2,4-bis-{4-(2-ethylhexyloxy)-2-hydroxy]-phenyl}-6-(4-methoxyphenyl)-1,3,5-triazine, methylene bis-benzotriazolyl tetramethylbutylphenol, terephthalylidene dicamphor sulfonic acid, diethylhexyl 2,6-naphthalate, digalloyltrioleate, ethyl 4-[bis(hydroxypropyl)]aminobenzoate, glycerol p-aminobenzoate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl)-5-sulfoniobenzoxazoic acid, and mixtures or combinations thereof.

Although organic or chemical sunscreens can be used in the topical composition of the present invention, it is not necessary to include them since the combination of inorganic sunscreen particles (e.g., $TiO_2$ and/or $ZnO$) with the alkoxylated diphenylacrylate compound provides a sufficient photoprotective barrier for blocking the harmful UV-A and UV-B radiation. Preferably, the topical composition of the present invention is substantially free of any organic or chemical sunscreens, and more preferably free of dibenzoylmethane derivatives, such as Avobenzone.

The inorganic particulate materials and the alkoxylated diphenylacrylate compound of the present invention can be added directly to any pharmaceutically or cosmetically acceptable carrier to form a cosmetic or topical composition. For purpose of the present invention, pharmaceutically or cosmetically acceptable carriers are substances that are biologically compatible with human skin and can be used to formulate active ingredients described hereinabove and/or hereinafter into a cream, gel, emulsion, liquid, suspension, powder, nail coating, skin oil, or lotion that can be topically applied. In the case where the cosmetically acceptable carrier is in the form of an emulsion, it may contain from about 0.1 to 99%, preferably from about 0.5 to 95%, more preferably from about 1 to 80% by weight of the total composition of water and from about 0.1 to 99%, preferably from about 0.1 to 80%, more preferably from about 0.5 to 75% by weight of the total composition of oil. In case where the composition is anhydrous it may comprise from about 0.1 to 90 wt % of oil and from about 0.1 to 75 wt % of other ingredients such as pigments, powders, non-aqueous solvents (such as mono-, di-, or polyhydric alcohols, etc. In case where the composition is in the form of an aqueous based gel, solution, or suspension, it may comprise from about 0.1 to 99 wt % of water and from about 0.1 to 75 wt % of other ingredients such as botanicals, non-aqueous solvents, etc.

Suitable components of the pharmaceutically or cosmetically acceptable carrier include, but are not limited to: moisturizing agents, astringent agents, chelating agents, sequestrants, emulsifiers/surfactants, emollients, preservatives, stabilizers, abrasives, adsorbents, thickeners, gellants, solidifying/structuring agents, anti-caking agents, anti-foaming agents, pH buffering/adjusting agents, binders, film formers, humectants, pigments, opacifiers, essential oils, fragrances, and aromatic compounds. The pharmaceutically or cosmetically acceptable carrier or carriers can be present in the topical or cosmetic composition of the present invention at an amount ranging from about 1% to about 99.9%, preferably from about 50% to about 99.5%, more preferably from about 70% to about 99%, and most preferably from about 80% to 90% by total weight of the topical or cosmetic composition.

The topical or cosmetic composition may contain one or more skin care additives, which are agents that provide benefits to the skin, rather than merely improving the physical or aesthetic characteristics of the topical composition. If present, such skin care actives may range from about 0.01 to 50%, preferably from about 0.05 to 35% by weight of the total composition. Exemplary skin care additives that can be used in the topical or cosmetic compositions of the present invention include, but are not limited to: self-tanning agents (e.g. dihydroxyacetone), anti-aging agents, DNA-repair enzymes, anti-wrinkle agents, anti-acne agents (e.g., resorcinol, salicylic acid, and the like), enzyme-inhibiting agents, collagen-stimulating agents, agents for the eradication of age spots and keratoses, analgesics, anesthetics, antimicrobials (e.g., antibacterials, antiyeast agents, antifungal agents, and antiviral agents), antidandruff agents, antidermatitis agents, antipruritic agents, antiemetics, anti-inflammatory agents, antihyperkeratolytic agents, antiperspirants, antipsoriatic agents, antiseborrheic agents, antihistamine agents, skin lightening agents, depigmenting agents, skin soothing/healing agents (e.g., aloe vera extract, allantoin, and the like), corticosteroids, hormones, antioxidants, proteins or peptides, vitamins and derivatives thereof (e.g., vitamin A, vitamin E, vitamin $B_3$, vitamin $B_5$, and the like), exfoliants, retinoids (e.g., retinoic acid and retinol), farnesol, bisabolol, phytantriol, glycerol, urea, guanidine (e.g., amino guanidine), clotrimazole, ketoconazole, miconozole, griseofulvin, hydroxyzine, diphenhydramine, pramoxine, lidocaine, procaine, mepivacaine, monobenzone, erythromycin, tetracycline, clindamycin, meclocyline, minocycline, hydroquinone, naproxen, ibuprofen, theophylline, cromolyn, albuterol, topical steroids (e.g., hydrocortisone, hydrocortisone 21-acetate, hydrocortisone 17-valerate, and hydrocortisone 17-butyrate), betamethasone valerate, betamethasone diproprionate, benzoyl peroxide, crotamiton, propranolol, promethazine, and mixtures or derivatives thereof. In a preferred, but not necessary embodiment of the present invention, the topical composition comprises one or more skin care actives selected from the group consisting of self-tanning agents, anti-aging agents, DNA repair enzymes, anti-wrinkle agents, anti-acne agents, antimicrobials, anti-inflammatory agents, skin-lightening agents, antioxidants, proteins or peptides, vitamins and derivatives thereof, exfoliants, and mixtures thereof.

For example, the topical or cosmetic compositions of the present invention may include one or more antioxidants, and more preferably one or more water-soluble extracts of biological materials that exhibit anti-oxidant activities. If present, such antioxidants or water-soluble extracts with anti-oxidant activities may range from about 0.01 to 45%, preferably from about 0.05 to 20%, more preferably from about 0.1 to 15% by weight of the total composition. Examples of suitable water-soluble extracts that exhibit anti-oxidant activities include, but are not limited to, extracts from: *artemia*, phytosphingosine, *polygonum cuspidatum* root, yeast such as *saccharomyces* lysate, *thermos thermophillus* ferment, birch (*Betula alba*), *mimosa tenuiflora* (bark) extract, fruit, clove, rye, malt, corn, spelt, millet, barley, oat, wheat, sesame, cumin, turmeric, green onion, celery, ginseng, ginger, licorice, carrot, bupleurum root, *Ginkgo biloba* (gingko), Foeniculi Fructus (fennel), kiwi, berry such as *Morus bombycis* (mulberry), *Gentiana lutea* (gentian), algae such as red algae, *Arctium lappa* (burdock), *Salvia officinalis* (sage), *Lentinus edodes* (shiitake mushroom), *Perilla frutescens* (perilla), *Filipendula Multijuga, Fucus vesiculosis* (bladderwrack, sea weed), peach kernel, *Allium sativum* (garlic), *Poria cocos* (poria), *Humulus lupulus* (hops), Mutan Cortex (*Moutan* Bark), *Pimpinella major, Lactuca sative* (lettuce), *Astragalus membranaceous* (*astragalus*) and *Rosmarinus officinalis* (rosemary), *Prunus amygdalus* (almond), *Althea officinale* (althea), aloe, Rosae Fructus (rose fruit, or *Rosa multiflora*), *Scuttelaria baicalensis* (Huang qin), Puerariae Radix (*Pueraria* Root, or *Pueraria lobata*), chamomile such as Chamomillae Flos (German chamomile), *Gardenia jasminoides* (zhii zi, Gardeniae Fructus), *Sophora flavescens* Aiton (Sophorae Radix), chlorella, rice bran, Paeoniae lactiflora (white peony), ziyu (*Sanguisorba officinalis*, burnet), *Morus alba* (sang bai pi, mulberry), *Glycine max* (soybean), *Camellia sinensis* (tea), Carthami Flos (safflower), *Aesculus hippocastanum* (horse chestnut), *Melissa officinalis* (lemon balm) and Coicis Semen (*Coix lacryma-jobi* var. *ma-yuen*), *Angelica keisukei*, *Arnica montana* (*arnica*), *Foeniculum officinale* (fennel), *Isodon japonicus* Hara (Isodonis Herba), *Daucus Carota* (carrot), *Oryza sativa* (rice), *Crataegus cuneata* (Japanese howthorn), *Acorus calamus* (sweet flag), *Crataegus oxycantha* (howthorn), *Juniperus communis*, *Ligusticum wallichii* (Chinese lovage), Swertiae Herba (*Swertia* Herb), *Thymus vulgaris* (garden thyme), *Citrus reticulata* (*Citrus unshiu*), *Capsicum* tincture, Angelicae sinensis (*angelica*), Aurantii Pericarpium (bitter orange peel), Ruscus aculeatus (butcher's bloom), *Vitis vinifera* (grape), Tilia japonica (lime), Citrus junos and *Rosa canina* (rose hip), caffeine, Cinnamomi Cortex (cinnamon bark) and *Eriobotrya japonica* Lindl. (loquat), Gambir, *Echinacea*, Phellodendri Cortex (amur cork tree or Phellodendron amurense), *Hypericum perforatum* (St. John's wort), *Citrus sinensis* (orange), *Valeriana fauriei* Briquet, *Artemisia capillaris* Thunb., *Cucumis sativus* (cucumber), Geranii Herba (*Geranium* Herb), *Lithospermum erythrorhizon* Sieb. et Zucc., *Hedera helix*, *Achillea millefolium* (yarrow), Ziziphus jujuba (Chinese dates), *Calendula officinalis* (pot marigold), *Houttuynia cordata* (Houttuyniae Herba, *Houttuynia* Herba), *Potentilla erecta*, *Petroselinum crispum* (parsley), *Parietaria officinalis*, *Santalum album* (sandalwood), *Prunus persica* (peach), *Centaurea cyanus* (cornflower), *Eucalyptus globulus* (eucalyptus) and *Lavandula angustifolia* (lavender), *Persea americana* (avocado), *Nasturtium officinalis* (watercress), *Symphytum officinale* (comfrey), *Asarum sieboldii* (wild ginger), *Xanthoxyum piperitum* (Japan pepper), *Rehmannia glutinosa* (di huang), *Mentha piperita* (peppermint), *Syzygium aromaticum* (clove), *Tussilago farfara* (coltsfoot) and *Haematoxylum campechianum* (logwood); Oolong tea, *Cinchona succirubra* (peruvian bark), *Betula verrucosa* (birch) and *Glechoma hederacea* (ground ivy), milk and royal jelly, honey, cysteine and derivatives thereof, ascorbic acid and derivatives thereof, BHA, BHT, ferulic acid and derivatives thereof, grapeseed extract, pine bark extract, horseradish extract, hydroquinones, rosmarinic acid, coffee robusta seed, caffeic acid, tocopherol and derivatives thereof, green tea extract, sodium DNA, sodium ribonucleic acid, octyl, propyl and dodecyl gallates, uric acid and thiodiproprionate derivatives.

For another example, the topical or cosmetic compositions of the present invention may include one or more DNA repair enzymes and more preferably one or more DNA repair enzymes selected from the group consisting of 8-oxoguanine DNA glucosylase, uracil-and-hypoxanthine-DNA-glycosylase, damaged-base glycosylase (e.g., 3-methyl-ladenine-DNA glycosylase), 3-methyladenine-DNA-glycosylase, pyrimidine dimer-specific glycosylase, pyrimidine glycosylase/abasic lyase, N-glycosylase/apyrimidinic lyase, N-glycosylase/apurinic-apyrimidinic lyase, photolyase, $O^6$-methylguanine-DNA-methyl transferase, T4 endonuclease V, pyrimidine dimer-specific endonuclease, apyrimidin/apurin-endonuclease, UV damage endonuclease, correndonuclease, and DNA exonuclease. Other DNA repair enzymes or enzyme complexes involved in either the base excision repair (BER) pathway, the nucleotide excision repair (NER) pathway, or the alternative excision repair pathway can also be used for practice of the present invention. Such DNA repair enzymes may be derived or extracted from suitable sources, such as bacteria, algae, protozoans, planktons, plants, and the like. Further, the DNA repair enzymes may be encapsulated in liposomes for more efficient delivery to the skin. Liposomes are microscopic vesicles consisting of an aqueous core enclosed in one or more lipid layers formed by membrane lipids, such as phospholipids and sphingomyelins. Liposomes facilitate transfer of skin care actives into the dermis of skin. For more details regarding encapsulation of DNA repair enzymes in liposomes, see U.S. Pat. No. 5,296,231, the contents of which are incorporated herein by reference in their entireties for all purposes. If present, the DNA repair enzymes may range from about 0.01% to 20%, preferably from about 0.1% to about 10%, and more preferably desirably from about 0.5% to about 2%, by total weight of the composition.

The cosmetically acceptable carrier may also contain one or more oils, which are also known as skin conditioning agents, such as volatile or nonvolatile silicones, esters, paraffinic hydrocarbons, vegetable oils, and synthetic oils. Suitable volatile or non-volatile silicones include, but are not limited to: cyclomethicone; methyl trimethicone; octamethyltrisiloxane; decamethyltetrasiloxane; dodecamethylpentasiloxane; dimethicone; phenyl trimethicone trimethylsiloxyphenyl dimethicone; phenyl dimethicone; cetyl dimethicone; dimethicone copolyol, cetyl dimethicone copolyol; glycerolated silicones such as lauryl PEG-9 polydimethylsiloxyethyl dimethicone; or mixtures thereof. In one embodiment, the composition may contain one or more non-volatile silicone oils having a viscosity ranging from about 5 to 250,000 cst at 25° C. Examples include dimethicone, phenyl trimethicone, diphenyl dimethicone, and the like. Suitable esters include mono-, di-, or triesters. Monoesters are in the general form, RCO—R' wherein R and R' are each independently a $C_{1-45}$ straight or branched chain, saturated or unsaturated alkyl. Diesters may be formed by the reaction of a $C_{1-45}$ aliphatic or aromatic mono- or dihydric alcohol with a $C_{1-45}$ aliphatic or aromatic mono- or dicarboxylic acid, as appropriate, where the aliphatic group may be straight or branched chain, or saturated or unsaturated. Suitable triesters include the reaction products of a $C_{1-45}$ aliphatic or aromatic alcohol having at least three hydroxyl groups with a $C_{1-45}$ carboxylic acid, or a $C_{1-45}$ aliphatic or aromatic alcohol with a $C_{1-45}$ tricarboxylic acid, with the aliphatic chains being linear or branched, saturated or unsaturated. Examples include esters of caprylic and capric acids and glycerin such as caprylic/capric triglycerides; esters of glycerin or polyglycerin and stearic acid such as glyceryl stearate, diglyceryl diisostearate; esters of malic acid and isostaryl alcohol such as diisostearyl malate; coco caprylate caprate and the like. If present, such oils may range from about 0.1 to 99% by total weight of the composition.

The cosmetically acceptable carrier may also comprise one or more humectants, which include, but are not limited to: glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Preferably, the humectants used in the composition of the invention are $C_{1-6}$, preferably $C_{2-4}$ alkylene glycols, most particularly butylene glycol, or glycerin. If present, such humectants may range from about 0.001% to about 25%, preferably from about 0.005% to about 20%, more preferably from about 0.1% to about 15%, by total weight of the topical composition.

The cosmetically acceptable carrier may also comprise one or more organosiloxane elastomers, generally those known as non-emulsifying. If present, such elastomers may range from about 0.1 to 30% by weight of the total composition. Examples of suitable elastomers include, but are not limited to dimethicone/vinyl dimethicone crosspolymer, methylvinylsiloxanes, methylvinylsiloxane-dimethylsiloxane copolymers, dimethylvinylsiloxy-terminated dimethylpolysiloxanes, dimethylvinylsiloxy-terminated dimethylsiloxane-methylphenylsiloxane copolymers, dimethylvinylsiloxy-terminated dimethylsiloxane-diphenylsiloxane-methylvinylsiloxane copolymers, trimethylsiloxy-terminated dimethylsiloxane-methylvinylsiloxane copolymers, trimethylsiloxy-terminated dimethylsiloxane-methylphenylsiloxane-methylvinylsiloxane copolymers, dimethylvinylsiloxy-terminated methyl(3,3,3-trifluoropropyl)polysiloxanes, and dimethylvinylsiloxy-terminated dimethylsiloxane-methyl(3,3,-trifluoropropyl)siloxane copolymers, and the like.

The composition may also contain one or more surfactants, particularly if present in the emulsion form. Preferably, such surfactants are nonionic and may be in the form of silicones or organic nonionic surfactants. Suggested ranges are from about 0.1 to 40%, preferably from about 0.5 to 35%, more preferably from about 1 to 30% by weight of the total composition. Suitable silicone surfactants include polyorganosiloxane polymers that have amphiphilic properties, for example contain hydrophilic radicals and lipophilic radicals. These silicone surfactants may be liquids or solids at room temperature. Exemplary silicone surfactants that can be used in the present invention include, but are not limited to: dimethicone copolyols, alkyl dimethicone copolyols, and emulsifying silicone elastomers. Emulsifying silicone elastomers are elastomers that have one or more hydrophilic groups such as hydroxyl, oxyethylene, and the like bonded thereto so as to confer hydrophilic properties to the elastomer.

Suitable organic nonionic surfactants may include alkoxylated alcohols or ethers formed by the reaction of an alcohol with a polyalkyleneoxide containing repeating units of alkylene oxide. Preferably, the alcohol is a fatty alcohol having 6 to 30 carbon atoms. Examples of organic nonionic surfactants that can be used in the present invention include, but are not limited to: steareth 2-100, beheneth 5-30, ceteareth 2-100, ceteth 1-45, and the like, which are formed by polyethyleneoxide with the corresponding stearyl/behenyl/cetyl alcohol (wherein the number as used herein designates the number of repeating units of ethylene oxide in the polyethyleneoxide). Other alkoxylated alcohols include esters formed by reaction of polymeric alkylene glycols with glyceryl fatty acid, such as PEG glyceryl oleates, PEG glyceryl stearate; or PEG polyhydroxyalkanotes such as PEG dipolyhydroxystearate wherein the number of repeating ethylene glycol units ranges from 3 to 1000.

Also suitable as nonionic surfactants are compounds formed by the reaction of a carboxylic acid with an alkylene oxide or polymeric ether. Monomeric, homopolymeric, or block copolymeric ethers, alkoxylated sorbitan, alkoxylated sorbitan derivatives can also be used as nonionic surfactants in the present invention.

The compositions of the invention may also contain other ingredients such as structuring agents in the form of polymeric structuring agents such as acrylic polymers, polyamides or polyurethanes. The structuring agents may be water or oil soluble or dispersible. Such structuring agents will provide structure, or increase the viscosity of the composition. If present, suggested ranges are from about 0.1 to 50%, preferably from about 0.5 to 40%, more preferably from about 1 to 35% by weight of the total composition. Suitable structuring agents include natural, synthetic waxes, or mineral waxes such as petrolatum, candelilla, ozokerite, synthetic wax, polyethylene, silicone waxes such as stearyl or behenyl dimethicone, and the like. Suitable polymeric structuring agents include carbomer, acrylic polymers or copolymers, such as acrylates copolymer, polyacrylate-1 crosspolymer, acrylates/C10-30 alkyl acrylate crosspolymer, C10-30 alkyl acrylate crosspolymer (e.g., those commercially available as Carbopol® or Pemulen®), ester or amide terminated polyamides (those commercially available from Arizona Chemical under the Uniclear® or Sylvaclear®), or aqueous dispersions or solutions of polyurethanes.

The topical compositions of the present invention, especially the sunscreen compositions, are preferably water-resistant, sweat-proof, non-irritating, non-comedogenic (i.e., will not clog pores), and/or hypo allergenic. More preferably, the topical compositions are transparent or translucent, non-whitening, and can be easily absorbed into the skin. Most preferably, the topical compositions provide maximum, broad spectrum photoprotection and a therapeutic or curative benefit for sun-damaged or photosensitive skin and will have an SPF ranging from about 15 to 100, preferably from about 20 to 75.

The topical compositions of the present invention are designed so that they may be worn daily and may be worn under make-up. Because in one embodiment of the invention the topical compositions of the present invention may contain relatively lower concentrations of organic chemical sunscreen agents, they are often perceived as more desirable to consumers who prefer sunscreens that do not have organic sunscreen compounds in them. Preferably, the compositions may be topically applied to any portion of the skin that will be or will tend to be exposed to UV irradiation, including, but not limited to, the face, the ears, the scalp, the hands, arms, shoulders, legs, feet, abdomen and back, and any area of the skin that an individual chooses to expose to UV, visible, and/or IR irradiation. Such UV irradiation is typically, but not necessarily, directed to the skin from the sun. Other UV, visible, and IR range light sources include most typical UV light sources, as will be appreciated by those of skill in the art, and also including most industrial light sources.

EXAMPLES

The following examples are illustrative, but not limiting, of the topical compositions of the present invention as described hereinabove.

Example I

In Vitro Measurements of Photo-Protective Effect in UVB and UVA Regions

Three (3) formulas were prepared by simply mixing the following ingredients:

| Ingredients | Concentration (wt %) | | |
| --- | --- | --- | --- |
| | A | B | C |
| De-ionized water | QS | QS | QS |
| Alcohol (Denatured) | 2.00 | — | 2.00 |
| Hydroxyethylcellulose | 1.38 | 1.38 | 1.38 |
| Hydroxypropyl methylcellulose | 0.72 | 0.72 | 0.72 |
| Ethylhexyl methoxycrylene ("Methoxycrylene") | 2.00 | — | 2.00 |
| Titanium dioxide/alginic acid/ aluminum hydroxide/hydrated silica | — | 4.00 | 4.00 |

UV-absorption spectra of the above-listed three (3) formulas, which spanned across a wavelength range of from about 290 nm to about 400 nm and covered both the UVB and UVA spectral regions, were measured by a UV spectrophotometer commercially available from Optometrics Corporation (Ayer, Mass.), hereinafter referred to as the SPF-290S analyzer. Specifically, a 3M™ Transpore™ tape was mounted onto a plastic template with a hole of about 2.5 cm in diameter. Each formula was dotted onto the test area of the tape (i.e., above the hole) and spread evenly to form a sample coating layer of about 2.0 mg/cm$^2$. The coating was dried for about 20 minutes at room temperature. The plastic template with the dried sample coating layer was then placed onto the horizontal sample area of the SPF-290S analyzer, and an Atlas Suntest XLS solar simulator manufactured by Atlas Material Testing Solutions (Chicago, Ill.) was used as the UV source to provide UV and near-UV radiation of from about 290 nm to 400 nm. UV absorption spectrum of each sample coating layer was measured by the SPF-290S analyzer, and four (4) measurements were conducted for each sample formula and then averaged to obtain an average UV absorption curve for each sample formula. The areas under such average UV absorption curve in the UVB region (290 nm-320 nm) and the UVA region (320 nm-400 nm) were calculated for each sample formula and are listed herein as follows:

TABLE I

| Formula | UVB Absorption Area | UVA Absorption Area |
|---|---|---|
| A | 10.8 | 13.0 |
| B | 38.5 | 19.7 |
| C | 56.9 | 38.7 |

It is clear from the above table that Formula C, which contained both Methoxycrylene and TiO$_2$, had an UVB absorption area (i.e., 56.9) that was greater than the sum of the UVB absorption area measured for Formula A (i.e., 10.8) containing only Methoxycrylene without TiO$_2$, and the UVB absorption area measured for Formula B (i.e., 38.5) containing only TiO$_2$ without Methoxycrylene. Further, Formula C had an UVA absorption area (i.e., 38.7) that was greater than the sum of the UVA absorption area measured for Formula A (i.e., 13.0) and the UVA absorption area measured for Formula B (i.e., 19.7). Therefore, it seems that the combination of Methoxycrylene with TiO$_2$ synergistically enhances the photo-protective effects of TiO$_2$ both in the UVA and UVB regions.

Example II

Two topical sunscreen compositions containing about 3.88% titanium dioxide and 5% zinc oxide in combination with 3% methoxycrylene were prepared by simply mixing the following ingredients:

| | Concentration (wt %) | |
|---|---|---|
| Ingredients | Formula 3 | Formula 4 |
| De-ionized water | QS | QS |
| Methyl trimethicone | 12.60 | 12.60 |
| Zinc oxide | 5.00 | 5.00 |
| C$_{12}$-C$_{15}$ alkyl benzoate | 4.35 | 4.35 |
| Isostearic acid | 0.40 | 0.40 |
| Polyhydroxystearic acid | 0.25 | 0.25 |
| Butylene glycol | 6.00 | 6.03 |
| Titanium dioxide | 3.88 | 3.88 |

-continued

| | Concentration (wt %) | |
|---|---|---|
| Ingredients | Formula 3 | Formula 4 |
| Dimethicone | 3.79 | 3.79 |
| Neopentyl glycol diethylhexanoate | 3.46 | 3.46 |
| Beeswax | 3.00 | 3.00 |
| Polydiethylsiloxane | 3.00 | 3.00 |
| Ethylhexyl methoxycrylene ("Methoxycrylene") | 3.00 | 3.00 |
| Isododecane | 2.18 | 2.18 |
| Disteardimonium hectorite | 0.24 | 0.24 |
| Propylene carbonate | 0.09 | 0.09 |
| Glycerin | 2.00 | 2.00 |
| Dimethicone/PEG-10/15 crosspolymer | 0.50 | 0.50 |
| Lauryl PEG-9 polydimethylsiloxyethyl dimethicone | 2.00 | 2.00 |
| Ethyl macadamiate | 2.00 | 2.00 |
| Dimethicone/vinyl dimethicone crosspolymer | 0.15 | 0.15 |
| Phenoxyethanol | 0.83 | 0.83 |
| Caprylyl glycol | 0.49 | 0.49 |
| Trimethylsiloxysilicate | 0.33 | 0.33 |
| Magnesium sulfate | 1.00 | 1.00 |
| Cetyl PEG/PPG-10/1 dimethicone | 1.00 | 1.00 |
| Iron oxides | 0.49 | 0.49 |
| Xanthan gum | 0.25 | 0.25 |
| Pantethine | 0.16 | 0.16 |
| Tocopheryl acetate | 0.20 | 0.20 |
| Alcaligenes polysaccharides | 0.20 | — |
| Lecithin | 0.01 | 0.01 |
| Hydrolyzed wheat protein/PVP crosspolymer | — | 0.40 |
| Dipentaerythrityl tri-polyhydroxystearate | — | 2.00 |
| Polyvinyl acetate | — | 0.35 |
| Acrylates/hydroxyesters acrylates copolymer | — | 0.16 |
| Acrylates copolymer | — | 0.30 |
| Silicone modified acryl resin | — | 0.50 |

Example III

Two additional topical sunscreen compositions containing about 3.92% titanium dioxide and 5% zinc oxide in combination with 2% methoxycrylene were prepared by simply mixing the following ingredients:

| | Concentration (wt %) | |
|---|---|---|
| Ingredients | Formula 1 | Formula 2 |
| De-ionized water | QS | QS |
| Methyl trimethicone | 12.60 | — |
| Butylene glycol | 6.03 | 3.00 |
| Zinc oxide | 5.00 | 5.00 |
| C$_{12}$-C$_{15}$ alkyl benzoate | 4.35 | 4.35 |
| Titanium dioxide (sunscreen grade) | 3.92 | 3.92 |
| Dimethicone | 3.68 | — |
| Beeswax | 3.00 | 3.00 |
| Polydiethylsiloxane | 3.00 | 3.00 |
| Neopentyl glycol diethylhexanoate | 3.00 | — |
| Dipentaerythrityl tri-polyhydroxystearate | 2.00 | 0.85 |
| Ethylhexyl methoxycrylene ("Methoxycrylene") | 2.00 | 2.00 |
| Glycerin | 2.00 | 3.00 |
| Lauryl PEG-9 polydimethylsiloxyethyl dimethicone | 2.00 | 1.00 |
| Ethyl macadamiate | 2.00 | — |
| Aleurites moluccana (Kukui) seed oil | 2.00 | — |
| Titanium dioxide (pigment grade) | 1.48 | 1.48 |
| Cetyl PEG/PPG-10/1 dimethicone | 1.00 | — |
| Magnesium sulfate | 1.00 | — |
| Phenoxyethanol | 0.83 | 0.31 |
| Trioctyldodecyl citrate | 0.55 | 0.20 |
| Caprylyl glycol | 0.49 | 0.47 |
| Dimethicone/PEG-10/15 crosspolymer | 0.48 | — |
| Hydrolyzed wheat protein/PVP crosspolymer | 0.40 | — |
| Isostearic acid | 0.40 | 0.40 |

-continued

| Ingredients | Concentration (wt %) | |
|---|---|---|
| | Formula 1 | Formula 2 |
| Iron oxides | 0.40 | 0.15 |
| Polyvinyl acetate | 0.35 | — |
| Trimethylsiloxysilicate | 0.33 | — |
| Acrylates copolymer | 0.30 | — |
| Aluminum hydroxide | 0.28 | 0.28 |
| Hydrated silica | 0.26 | 0.26 |
| Polyhydroxystearic acid | 0.25 | 0.25 |
| Xanthan gum | 0.25 | 0.50 |
| Tocopheryl acetate | 0.20 | — |
| Acrylates/hydroxyesters acrylates copolymer | 0.16 | — |
| Pantethine | 0.16 | — |
| Dimethicone/vinyl dimethicone crosspolymer | 0.15 | — |
| Alginic acid | 0.06 | 0.06 |
| Dipropylene glycol | 0.01 | — |
| Lecithin | 0.01 | — |
| Tocopherol | 0.01 | — |
| Isononyl isononanoate | — | 10.00 |
| Caprylyl methicone | — | 5.00 |
| Mica | — | 5.00 |
| Polyester-8 | — | 3.00 |
| Stearyl heptanoate | — | 2.00 |
| Steareth-21 | — | 1.75 |
| Glyceryl stearate | — | 1.00 |
| Hydrogenated lecithin | — | 1.00 |
| Magnesium aluminum silicate | — | 0.60 |
| Cetyl alcohol | — | 0.50 |
| Trehalose | — | 0.50 |
| PEG-100 stearate | — | 0.50 |
| Steareth-2 | — | 0.30 |
| Disodium EDTA | — | 0.20 |
| Polyethylene | — | 0.20 |
| Propylene glycol dicaprate | — | 0.11 |
| Hexylene glycol | — | 0.09 |
| *Helianthus annuus* (sunflower) seedcake | — | 0.08 |
| Sodium hyaluronate | — | 0.02 |
| Magnesium ascorbyl phosphate | — | 0.01 |
| *Hordeum vulgare* (barley) extract | — | 0.01 |

While some illustrative embodiments of the inventions have been described hereinabove, such illustrative embodiments should not be interpreted in any manner to limit the broad scope of the prevent invention. Various modifications and equivalents of the described embodiments and components thereof will be apparent to those of ordinary skill in the art. Some modifications and equivalents will be readily recognized by one ordinarily skilled in the art, while others may require no more than routine experimentation. It is therefore understood that such modifications and equivalents are within the spirit and scope of the present invention.

What is claimed is:

1. A topical composition comprising at least one inorganic particulate material and an alkoxylated diphenylacrylate compound in a pharmaceutically or cosmetically acceptable carrier, wherein said at least one inorganic particulate material is entrapped by collapsed polymeric shells to form microspheres having an average particle size ranging from about 1 micron to about 50 microns.

2. The topical composition of claim 1, wherein the at least one inorganic particulate material comprises at least one metal oxide.

3. The topical composition of claim 1, wherein the at least one inorganic particulate material comprises a physical sunscreen agent selected from the group consisting of titanium dioxide particles, zinc oxide particles, and mixtures thereof.

4. The topical composition of claim 1, wherein the alkoxylated diphenylacrylate compound is an alkoxylated α-cyano-diphenylacrylate having the formula (I):

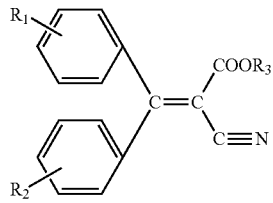

wherein one or both of $R_1$ and $R_2$ is a straight or branched-chain $C_1$-$C_{30}$ alkoxy radical, any non-alkoxy radical $R_1$ or $R_2$ is hydrogen, and $R_3$ is a straight or branched-chain $C_1$-$C_{30}$ alkyl radical.

5. The topical composition of claim 4, wherein one or both of $R_1$ and $R_2$ is a straight or branched-chain $C_1$-$C_8$ alkoxy radical.

6. The composition of claim 1, wherein the alkoxylated diphenylacrylate compound is an alkoxylated α-cyanodiphenylacrylate having the formula (III), (IV) or (V):

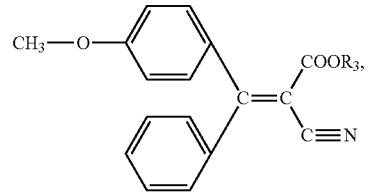

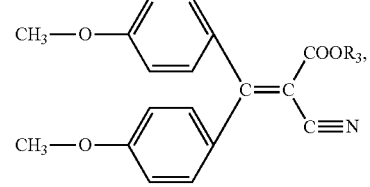

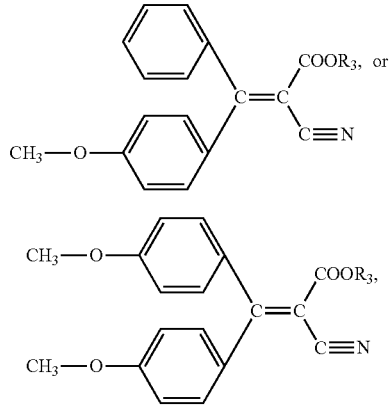

wherein $R_3$ is a straight or branched-chain $C_1$-$C_{30}$ alkyl radical.

7. The topical composition of claim 1, wherein the alkoxylated diphenylacrylate compound is α-ethylhexyl α-cyano-β-(4-methoxyphenyl)-β-phenylacrylate.

8. The topical composition of claim 1, further comprising at least one DNA repair enzyme.

9. The topical composition of claim 1, further comprising glycerin or a C2-C4 alkylene glycol.

10. The topical composition of claim 1, further comprising methyl trimethicone.

11. A topical composition having an SPF ranging from about 15 to 100 comprising α-ethylhexyl α-cyano-β-(4-methoxyphenyl)-β-phenylacrylate, and an inorganic particulate selected from the group consisting of zinc oxide, titanium dioxide, and mixtures thereof, wherein said inorganic particulate is entrapped by collapsed polymeric shells to form microspheres having an average particle size ranging from about 1 micron to about 50 microns.

12. The topical composition of claim 11, further comprising at least one nonvolatile silicone having a viscosity ranging from about 5 to 250,000 centistokes at 25° C.

13. The topical composition of claim 11, further comprising at least one silicone elastomer.

14. The topical composition of claim 11, further comprising trimethylsiloxysilicate.

15. The topical composition of claim 11, further comprising at least one volatile paraffinic hydrocarbon selected from the group consisting of isododecane, isohexadecane, and mixtures thereof.

* * * * *